United States Patent
Nichani et al.

(10) Patent No.: US 6,587,582 B1
(45) Date of Patent: *Jul. 1, 2003

(54) SEMICONDUCTOR DEVICE IMAGE INSPECTION WITH CONTRAST ENHANCEMENT

(75) Inventors: Sanjay J. Nichani, Natick, MA (US); Joseph Scola, Medfield, MA (US)

(73) Assignee: Cognex Corporation, Natick, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/924,902

(22) Filed: Aug. 8, 2001

Related U.S. Application Data

(63) Continuation of application No. 09/184,407, filed on Aug. 25, 1998, now Pat. No. 6,298,149, which is a continuation of application No. 08/621,189, filed on Mar. 21, 1996, now abandoned.

(51) Int. Cl.⁷ .................................................. G06T 5/50
(52) U.S. Cl. ..................................... 382/149; 356/237.4
(58) Field of Search ................................ 382/144, 145, 382/173, 221, 146, 101, 147, 102, 148, 149; 348/87, 126; 438/15, 16; 250/559.46, 559.4, 559.41, 559.45; 702/40, 159; 700/110; 356/237.4, 237.5, 338, 339

(56) References Cited

U.S. PATENT DOCUMENTS

| | | |
|---|---|---|
| 3,816,722 A | 6/1974 | Sakoe et al. |
| 3,936,800 A | 2/1976 | Ejiri et al. |
| 3,967,100 A | 6/1976 | Shimomura |
| 3,968,475 A | 7/1976 | McMahon |
| 3,978,326 A | 8/1976 | Shimomura |
| 4,011,403 A | 3/1977 | Epstein et al. |
| 4,115,702 A | 9/1978 | Nopper |
| 4,115,762 A | 9/1978 | Akiyama et al. |
| 4,183,013 A | 1/1980 | Agrawala et al. |
| 4,200,861 A | 4/1980 | Hubach et al. |

(List continued on next page.)

FOREIGN PATENT DOCUMENTS

| | | |
|---|---|---|
| EP | 0 527 632 A2 | 2/1993 |
| WO | WO 95/21376 | 8/1995 |
| WO | WO 95/122137 | 8/1995 |
| WO | WO 97/21189 | 6/1997 |
| WO | WO 97/22858 | 6/1997 |
| WO | WO 97/24692 | 7/1997 |
| WO | WO 97/24693 | 7/1997 |

OTHER PUBLICATIONS

Grimson, W. Eric L. and Huttenlocher, Daniel P., "On the Sensitivity of the Hough Transform for Object Recognition", May 1990, IEEE Transactions on Pattern Analysis and Machine Intelligence, vol. 12, No. 3.

Medina–Mora et al. (1981) An Incremental Programming Environment, IEEE Transactions on Software Eng. SE–7:472–482.

Teitelbaum et al. (19810 The Cornell Program Synthesizer: A Syntax–Directed Programming Environment, Communications of the ACM 24:563–573.

(List continued on next page.)

*Primary Examiner*—Brian Werner
(74) *Attorney, Agent, or Firm*—David Powsner; Russ Weinzimmer

(57) ABSTRACT

Machine vision methods for inspection of semiconductor die lead frames include the steps of generating a first image of the lead frame, generating a second image of the lead frame and any defect thereon, and subtracting the second image from the first image. The methods are characterized in that the second image is generated such that subtraction of it from the first image emphasizes the defect with respect to the lead frame.

15 Claims, 4 Drawing Sheets

U.S. PATENT DOCUMENTS

| | | |
|---|---|---|
| 4,254,400 A | 3/1981 | Yoda et al. |
| 4,286,293 A * | 8/1981 | Jablonowski ............... 358/199 |
| 4,300,164 A | 11/1981 | Sacks |
| 4,385,322 A | 5/1983 | Hubach et al. |
| 4,441,124 A | 4/1984 | Heebner et al. |
| 4,441,206 A | 4/1984 | Kuniyoshi et al. |
| 4,519,041 A | 5/1985 | Fant et al. |
| 4,534,813 A | 8/1985 | Williamson et al. |
| 4,541,116 A | 9/1985 | Lougheed |
| 4,570,180 A | 2/1986 | Baier et al. |
| 4,577,344 A | 3/1986 | Warren et al. |
| 4,581,762 A | 4/1986 | Lapidus et al. |
| 4,606,065 A | 8/1986 | Beg et al. |
| 4,617,619 A | 10/1986 | Gehly |
| 4,630,306 A | 12/1986 | West et al. |
| 4,668,982 A * | 5/1987 | Tinnerino ................... 358/101 |
| 4,688,088 A | 8/1987 | Hamazaki et al. |
| 4,706,168 A | 11/1987 | Weisner |
| 4,728,195 A | 3/1988 | Silver |
| 4,730,260 A | 3/1988 | Mori et al. |
| 4,731,858 A | 3/1988 | Grasmueller et al. |
| 4,736,437 A | 4/1988 | Sacks et al. |
| 4,742,551 A | 5/1988 | Deering |
| 4,758,782 A | 7/1988 | Kobayashi |
| 4,764,870 A | 8/1988 | Haskin |
| 4,771,469 A | 9/1988 | Wittenburg |
| 4,783,826 A | 11/1988 | Koso |
| 4,783,828 A | 11/1988 | Sadjadi |
| 4,783,829 A | 11/1988 | Miyakawa et al. |
| 4,831,580 A | 5/1989 | Yamada |
| 4,860,374 A | 8/1989 | Murakami et al. |
| 4,860,375 A | 8/1989 | McCubbrey et al. |
| 4,876,457 A | 10/1989 | Bose |
| 4,876,728 A | 10/1989 | Roth |
| 4,903,218 A | 2/1990 | Longo et al. |
| 4,907,169 A | 3/1990 | Lovoi |
| 4,914,553 A | 4/1990 | Hamada et al. |
| 4,922,543 A | 5/1990 | Ahlbom et al. |
| 4,926,492 A | 5/1990 | Tanaka et al. |
| 4,932,065 A | 6/1990 | Feldgajer |
| 4,953,224 A | 8/1990 | Ichinose et al. |
| 4,955,062 A | 9/1990 | Terui |
| 4,959,898 A | 10/1990 | Landman et al. |
| 4,962,423 A | 10/1990 | Yamada et al. |
| 4,972,359 A | 11/1990 | Silver et al. |
| 4,982,438 A | 1/1991 | Usami et al. |
| 5,012,402 A | 4/1991 | Akiyama |
| 5,012,524 A | 4/1991 | Le Beau |
| 5,038,048 A * | 8/1991 | Maeda et al. ............... 250/563 |
| 5,046,190 A | 9/1991 | Daniel et al. |
| 5,054,096 A | 10/1991 | Beizer |
| 5,060,276 A | 10/1991 | Morris et al. |
| 5,063,608 A | 11/1991 | Siegel |
| 5,073,958 A | 12/1991 | Imme |
| 5,081,656 A | 1/1992 | Baker et al. |
| 5,081,689 A | 1/1992 | Meyer et al. |
| 5,086,478 A | 2/1992 | Kelly-Mahaffey et al. |
| 5,090,576 A | 2/1992 | Menten |
| 5,091,861 A | 2/1992 | Geller et al. |
| 5,091,968 A | 2/1992 | Higgins et al. |
| 5,093,867 A | 3/1992 | Hori et al. |
| 5,113,565 A | 5/1992 | Cipolla et al. |
| 5,115,309 A | 5/1992 | Hang |
| 5,119,435 A | 6/1992 | Berkin |
| 5,124,622 A | 6/1992 | Kawamura et al. |
| 5,133,022 A | 7/1992 | Weideman |
| 5,134,575 A | 7/1992 | Takagi |
| 5,143,436 A | 9/1992 | Baylor et al. |
| 5,145,432 A | 9/1992 | Midland et al. |
| 5,151,951 A | 9/1992 | Ueda et al. |
| 5,153,925 A | 10/1992 | Tanioka et al. |
| 5,159,281 A | 10/1992 | Hedstrom et al. |
| 5,159,645 A | 10/1992 | Kumagai |
| 5,164,994 A | 11/1992 | Bushroe |
| 5,166,985 A * | 11/1992 | Takagi et al. ................... 382/8 |
| 5,168,269 A | 12/1992 | Harlan |
| 5,185,855 A | 2/1993 | Kato et al. |
| 5,189,712 A | 2/1993 | Kajiwara et al. |
| 5,206,820 A | 4/1993 | Ammann et al. |
| 5,216,503 A | 6/1993 | Paik |
| 5,225,940 A | 7/1993 | Ishii et al. |
| 5,230,027 A | 7/1993 | Kikuchi |
| 5,243,607 A | 9/1993 | Masson et al. |
| 5,253,306 A | 10/1993 | Nishio |
| 5,253,308 A | 10/1993 | Johnson |
| 5,265,173 A | 11/1993 | Griffin et al. |
| 5,271,068 A | 12/1993 | Ueda et al. |
| 5,287,449 A | 2/1994 | Kojima |
| 5,297,256 A | 3/1994 | Wolstenholme et al. |
| 5,299,269 A | 3/1994 | Gaborski et al. |
| 5,311,598 A | 5/1994 | Bose et al. |
| 5,315,388 A | 5/1994 | Shen et al. |
| 5,319,457 A | 6/1994 | Nakahashi et al. |
| 5,327,156 A | 7/1994 | Masukane et al. |
| 5,337,267 A | 8/1994 | Colavin |
| 5,363,507 A | 11/1994 | Nakayama et al. |
| 5,367,439 A | 11/1994 | Mayer et al. |
| 5,367,667 A | 11/1994 | Wahlquist et al. |
| 5,371,690 A | 12/1994 | Engel et al. |
| 5,388,197 A | 2/1995 | Rayner |
| 5,388,252 A | 2/1995 | Dreste et al. |
| 5,398,292 A | 3/1995 | Aoyama |
| 5,408,537 A * | 4/1995 | Major ........................... 382/8 |
| 5,432,525 A | 7/1995 | Maruo et al. |
| 5,440,699 A | 8/1995 | Farrand et al. |
| 5,455,870 A * | 10/1995 | Sepai et al. ................. 382/147 |
| 5,455,933 A | 10/1995 | Schieve et al. |
| 5,475,766 A | 12/1995 | Tsuchiya et al. |
| 5,477,138 A | 12/1995 | Erjavic et al. |
| 5,481,712 A | 1/1996 | Silver et al. |
| 5,485,570 A | 1/1996 | Bushboom et al. |
| 5,491,780 A | 2/1996 | Fyles et al. |
| 5,495,424 A | 2/1996 | Tokura |
| 5,495,537 A | 2/1996 | Bedrosian et al. |
| 5,519,840 A | 5/1996 | Matias et al. |
| 5,526,050 A | 6/1996 | King et al. |
| 5,532,739 A | 7/1996 | Garakani et al. |
| 5,550,763 A | 8/1996 | Michael |
| 5,566,877 A | 10/1996 | McCormack |
| 5,568,563 A | 10/1996 | Tanaka et al. |
| 5,574,668 A | 11/1996 | Beaty |
| 5,574,801 A | 11/1996 | Collet-Beillon |
| 5,583,949 A | 12/1996 | Smith et al. |
| 5,583,954 A | 12/1996 | Garakani |
| 5,592,562 A | 1/1997 | Rooks |
| 5,594,859 A | 1/1997 | Palmer et al. |
| 5,602,937 A | 2/1997 | Bedrosian et al. |
| 5,608,872 A | 3/1997 | Schwartz et al. |
| 5,640,199 A | 6/1997 | Garakani et al. |
| 5,640,200 A | 6/1997 | Michael |
| 5,724,439 A | 3/1998 | Mizuoka et al. |
| 5,859,698 A * | 1/1999 | Chau et al. ................. 356/237 |
| 5,917,935 A * | 6/1999 | Hawthorne et al. ......... 382/149 |

OTHER PUBLICATIONS

Newsletter from Acquity Imaging, Inc., "Remote Vision Support Package—The Phones Are Ringing!," 1 page.

PictureTel Corporation Product Brochure "PictureTel Live PCS 100(tm) Personal Visual Communications System," 3 pp. (1993).

PictureTel Corporation Product Brochure "PictureTel System 1000: Complete Videoconferencing for Cost Sensitive Applications," 4 pp. (1993).

PictureTel Corporation Product Brochure, "PictureTel System 4000(tm) A Family of Models to Fit Your Application from Offices to Boardrooms, Classrooms, and Auditoriums," 4 pp. (1993).

Symantec Corporation, "The Norton pcAnywhere User's Guide," Table of Contents 8 pp; Introduction of pcAnywhere Technology pp i–vii; Chapter 7—Sessions; pp. 191–240 (1991).

Bursky, Dave, "CMOS Four–Chip Set Process Images at 20–MHz Data Rates," Electronic Design, May 28, 1987, pp. 39–44.

Plessey Semiconductors, Preliminary Information, May 1986, Publication No. PS2067, May 1986, pp. 1–5.

NEC Electronics Inc., PD7281 Image Pipelined Processor, Product Information Brochure, pp. 2–169–2–211.

Horn, Berthold Klaus Paul. "Robot Vision", The Massachusetts Institute for Technology, 1986.

Rosenfeld, Azriel. "Computer Vision: Basic Principles," Proceedings of the IEEE. vol. 76, No. 8, Aug. 1988. pp. 863–868.

Rosenfeld, Azriel. "Computer Vision: Basic Principles". *Proceedings of the IEEE*, vol. 76, No. 8, Aug., 1988. pp. 863–868.

* cited by examiner (Object-to-Background Contrast:
Positive)

(Object-to-Background Contrast:
Negative)

(Object-to-Background Contrast:
Enhanced)

SEMICONDUCTOR DEVICE IMAGE INSPECTION WITH CONTRAST ENHANCEMENT

REFERENCE TO RELATED APPLICATIONS

This is a continuation of U.S. patent application Ser. No. 09/184,407 filed Aug. 25, 1998, now issued as U.S. Pat. No. 6,298,149, which is a continuation of U.S. patent application Ser. No. 08/621,189 filed Mar. 21, 1996, now abandoned.

This application is related to U.S. Pat. No. 6,259,827, entitled MACHINE VISION METHODS FOR ENHANCING THE CONTRAST BETWEEN AN OBJECT AND ITS BACKGROUND USING MULTIPLE ON-AXIS IMAGES, issued Jul. 10, 2001, the teachings of which are incorporated herein by reference.

This application is related to U.S. Pat. No. 5,949,901, entitled SEMICONDUCTOR DEVICE IMAGE INSPECTION UTILIZING IMAGE SUBTRACTION AND THRESHOLD IMAGING, issued Sep. 7, 1999, the teachings of which are incorporated herein by reference.

RESERVATION OF COPYRIGHT

The disclosure of this patent document contains material which is subject to copyright protection. The owner thereof has no objection to facsimile reproduction by anyone of the patent document or of the patent disclosure, as it appears in the United States Patent and Trademark Office patent file or records, but otherwise reserves all rights under copyright law.

BACKGROUND OF THE INVENTION

The invention pertains to machine vision and, more particularly, to methods for inspection of leads on semiconductor die packages (or lead frames).

At the heart of an integrated circuit is a semiconductor die. This is a wafer of semiconducting material (e.g., silicon) with hundreds of thousands or millions of electronic circuit components etched into its layers. To enhance processing speed and reduce power consumption, the dies are made as small as possible, e.g., less than a square-inch in area and several mils thick. To facilitate handling, the dies are glued into supporting frames, i.e., lead frames. In addition to providing stability, these frames have large conductive leads that can be soldered to other circuit components, e.g., on a printed circuit board. The leads are typically connected to corresponding pads on the die via a process called wire bonding, wherein a small conductive thread is bonded to each lead and its corresponding pad. Once a semiconductor die and its frame are assembled, they are typically packaged in a ceramic or plastic, forming an integrated circuit.

Inspection of the lead area of the semiconductor die packages is important in the semiconductor industry. Such inspection typically involves checking the leads on the package; both before and after the die is bonded to the package.

The most common defect in assembly is the deposit of unwanted adhesive on the leads. This is sometimes referred to as an AOL defect. Since the adhesive is conductive, it can effectively "short circuit" the semiconductor die's electronic functions.

The inspection of semiconductor packages for adhesive on leads has proven to be a vexing machine vision problem. This is a result of the complexity of the "background," i.e., the lead pattern which must be inspected in order to find the defect. This is further complicated by the decreasing size, and increasing number, of leads, as well as by the limited resolution of the cameras typically used for inspection. In this regard, it will be appreciated that while there are a variety of lead configurations, there are two basic types: etched leads and flying/free leads. The former are rigid and are etched onto a substrate, while the latter are mechanically pressed but non-rigid.

The prior art suggests the use of a technique referred to golden template comparison (GTC) to inspect the package leads. GTC is a technique for locating objects by comparing a feature under scrutiny (to wit, a lead frame) to a good image—or golden template—that is stored in memory. The technique subtracts the good image from the test image and analyzes the difference to determine if the expected object (e.g., a defect) is present. For example, upon subtracting the image of a good lead frame from a defective one, the resulting "difference" image would reveal an adhesive blotch that could be flagged as a defect.

Before GTC inspections can be performed, the system must be "trained" so that the golden template can be stored in memory. To this end, the GTC training functions are employed to analyze several good samples of a scene to create a "mean" image and "standard deviation" image. The mean image is a statistical average of all the samples analyzed by the training functions. It defines what a typical good scene looks like. The standard deviation image defines those areas on the object where there is little variation from part to part, as well as those areas in which there is great variation from part to part. This latter image permits GTC's runtime inspection functions to use less sensitivity in areas of greater expected variation, and more sensitivity in areas of less expected variation.

At runtime, a system employing GTC captures an image of a scene of interest. Where the position of that scene is different from the training position, the captured image is aligned, or registered, with the mean image. The intensities of the captured image are also normalized with those of the mean image to ensure that variations illumination do not adversely affect the comparison.

The GTC inspection functions then subtract the registered, normalized, captured image from the mean image to produce a difference image that contains all the variations between the two. That difference image is then compared with a "threshold" image derived from the standard deviation image. This determines which pixels of the difference image are to be ignored and which should be analyzed as possible defects. The latter are subjected to morphology, to eliminate or accentuate pixel data patterns and to eliminate noise. An object recognition technique, such as connectivity analysis, can then be employed to classify the apparent defects.

Although GTC inspection tools have proven quite successful, they suffer some limitations. For example, except in unusual circumstances, GTC requires registration—i.e., that the image under inspection be registered with the template image. GTC also uses a standard deviation image for thresholding, which can result in a loss of resolution near edges due to high resulting threshold values. GTC is, additionally, limited to applications where the images are repeatable: it cannot be used where image-to-image variation results form changes in size, shape, orientation and warping.

GTC is typically used to inspect only etched lead configurations, where it can be effectively used if the lead count is not high. Where that count is high, the frequency of etches results in a large area being effectively masked by the high standard deviation at the lead edges. GTC has not proven effective in inspections of flying/free configurations. Moreover, it is limited in that it requires excessive memory or processing time in instances where the package under inspection is rotated.

Blob analysis is also used to inspect etched lead configurations, as well as free-flying lead configurations. However, this analysis technique is only effective if the lead count is not high.

An object of this invention, therefore, is to provide improved methods for machine vision and, more particularly, improved methods for inspecting leads on semiconductor die packages or lead frames.

A further object is to provide such methods that can be used to identify defects such as adhesive blotches on those leads.

Yet another object is to provide such methods that can be used in inspecting the full range of die packages, including both etched lead packages and flying/free lead packages.

Yet still another object is to provide such methods that do not routinely necessitate alignment or registration of an image under inspection with a template image.

Still yet a further object of the invention is to provide such methods that do not require training.

Still other objects of the invention include providing such machine vision methods as can be readily implemented on existing machine vision processing equipment, and which can be implemented for rapid execution without excessive consumption of computational power.

SUMMARY OF THE INVENTION

The foregoing objects are among those achieved by the invention which provides, in one aspect, a machine vision method for inspecting leads on semiconductor die package, or lead frame. The method includes the steps of generating a first image of the lead frame (including, its leads and other structures—together, referred to as the "lead frame" or "background"), generating a second image of the lead frame and any defects thereon (e.g., excessive adhesive), and subtracting the second image from the first image. The method is characterized in that the second image is generated such that subtraction of it from the first image emphasizes the defect with respect to the background.

In related aspects of the invention, the second step is characterized as generating the second image such that its subtraction from the first image increases a contrast between the defect and the background. That step is characterized, in still further aspects of the invention, as being one that results in defect-to-background contrast differences in the second image that are of opposite polarity from the defect-to-contrast differences in the first image.

In further aspects, the invention calls for generating a third image with the results of the subtraction, and for isolating the expected defects on that third image. Isolation can be performed, according to other aspects of the invention, by conventional machine vision segmentation techniques such as connectivity analysis, edge detection and/or tracking, and by thresholding. In the latter regard, a threshold image—as opposed to one or two threshold values—can be generated by mapping image intensity values of the first or second image. That threshold image can, then, be subtracted from the third image (i.e, the difference image) to isolate further the expected defects.

Still further objects of the invention provide for normalizing the first and second images before subtracting them to generate the third image. In this aspect, the invention determines distributions of intensity values of each of the first and second images, applying mapping functions to one or both of them in order to match the tails of those distributions. The first and second images can also be registered prior to subtraction.

According to further aspects of the invention, the first and second images are generated by illuminating the lead frame with different respective light or emission sources. This includes, for example, illuminating it direct, on-axis lighting to generate the first image, and illuminating it with diffuse, off-access or grazing light to generate the second image.

Additional aspects of the invention provide methods incorporating various combinations of the foregoing aspects.

These and other aspects of the invention are evident in the drawings and in the descriptions that follow.

BRIEF DESCRIPTION OF THE DRAWINGS

A better understanding of the invention may be attained by reference to the drawings in which.

DETAILED DESCRIPTION OF THE ILLUSTRATED EMBODIMENT

Figure 1:
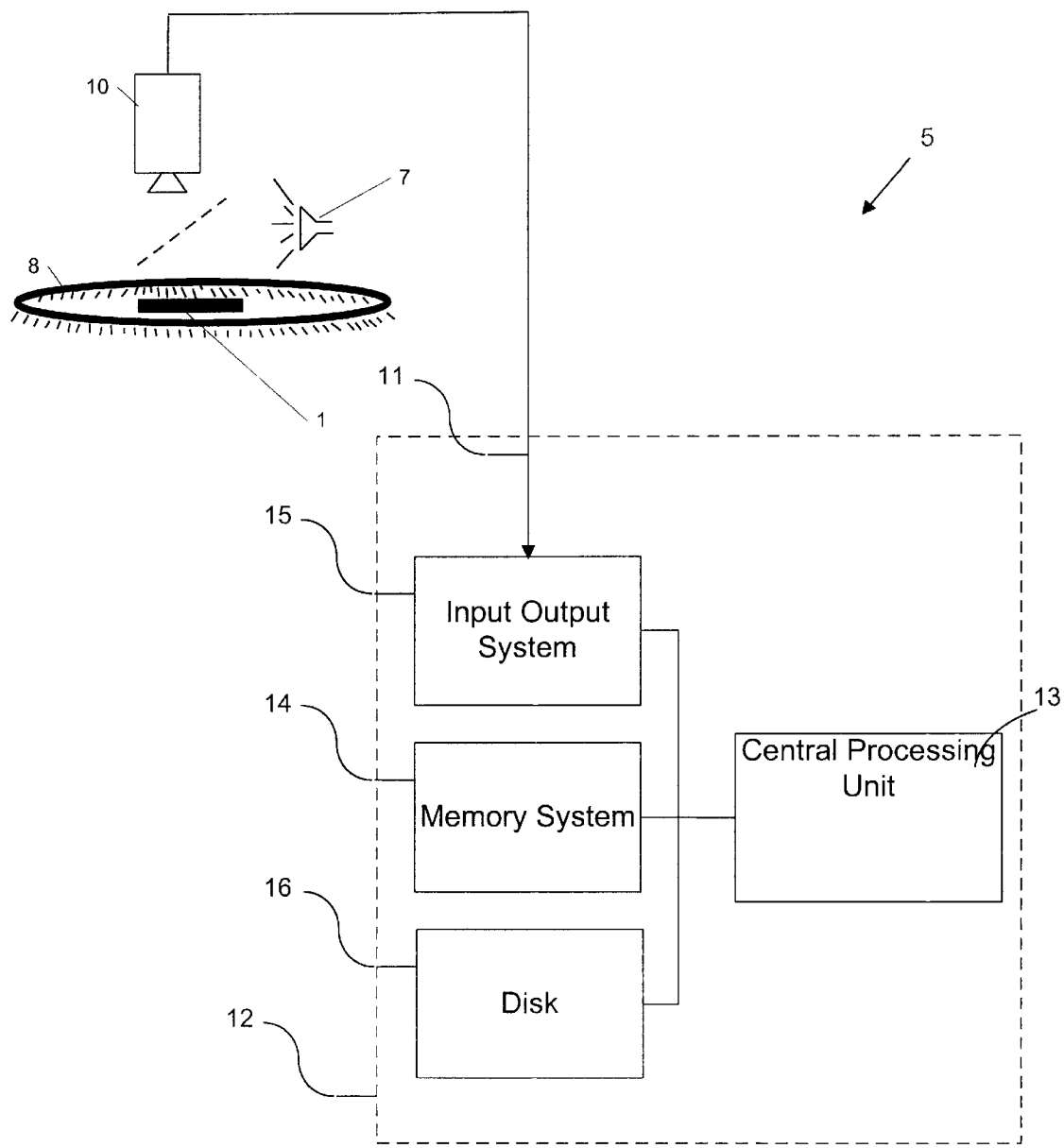
FIG. 1 depicts a machine vision system for practice of the invention.

FIG. 1 illustrates a system 5 for inspecting semiconductor die lead frames in accord with the invention. The system 5 includes a capturing device 10, such as a conventional video camera (such as the Sony XC75 camera with COSMICAR lens 50 mm lens) or scanner, that generates an image of a lead frame 1. Image data (or pixels) generated by the capturing device 10 represent, in the conventional manner, the image intensity (e.g., color or brightness) of each point in the scene at the resolution of the capturing device. The lead frame is illuminated by on-axis light 7 and ring light 8 for generation of multiple images that facilitate identification of defects in accord with methods discussed herein.

The digital image data is transmitted from capturing device 10 via a communications path 11 to an image analysis system 12. This can be a conventional digital data processor, or a vision processing system (such as the Cognex 5400) of the type commercially available from the assignee hereof, Cognex Corporation, programmed in accord with the teachings hereof to perform image segmentation. The image analysis system 12 may have one or more central processing units 13, main memory 14, input-output system 15, and disc drive (or other mass storage device) 16, all of the conventional type.

The system 12 and, more particularly, central processing unit 13, is configured by programming instructions according to the teachings hereof for image segmentation, as described in further detail below. Those skilled in the art will appreciate that, in addition to implementation on a programmable digital data processor, the methods and apparatus taught herein can be implemented in special purpose hardware.

Figure 2A:
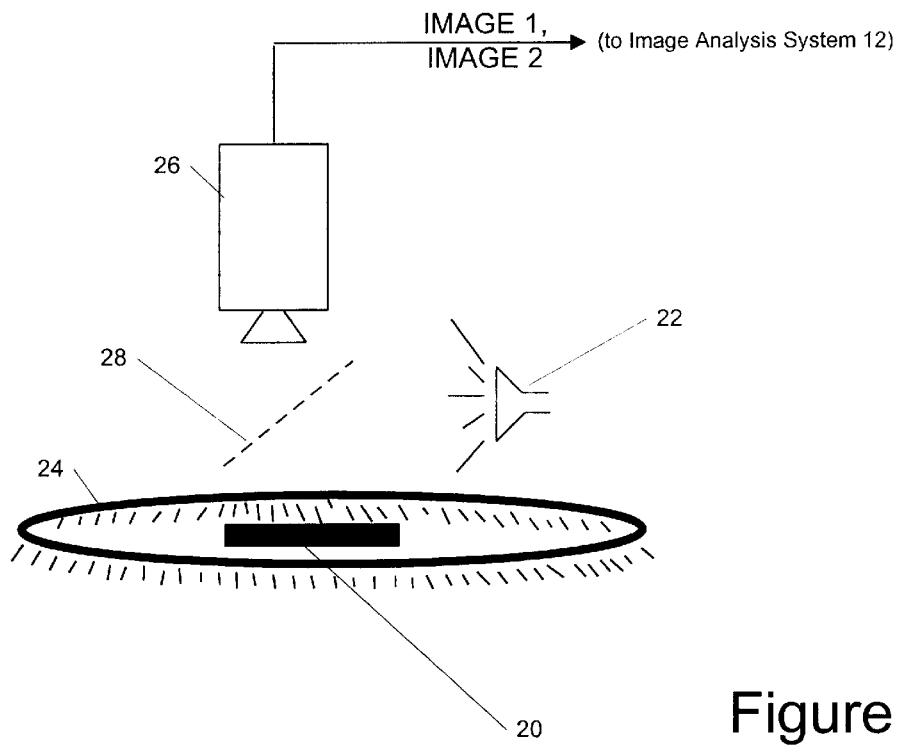
FIGS. 2A–2B depict illumination arrangements for generating images analyzed in accord with the invention.

FIG. 2A illustrates an arrangement of light sources according to the invention for on-axis and diffuse (or grazing) light illumination of lead frame 20. The arrangement includes lighting sources 22 and 24 positioned for illuminating lead frame 20. Lighting source 22 provides direct, on-axis lighting via reflection off a half-silvered, partially transparent, angled one-way mirror 28, while lighting source 24 provides diffuse, off-access lighting, or grazing light. Images of the illuminated frame 20 are captured by camera 26 through mirror 28.

Lighting source 22 is of the conventional type known in the art for on-axis illumination of objects under inspection in a machine vision application. A preferred such light is a diffused on-axis light (DOAL) commercially available from Dolan Jenner. The source 22 and mirror 28 are positioned to cause potential defects on the lead area of the frame 20 (e.g., adhesive patches) to appear as dark features against a light background.

Lighting source 24 is also of a conventional type known in the art for use in providing diffuse, off-axis light or grazing light in machine vision applications. One preferred source 24 is an arrangement of several point light sources, e.g., fiber optic bundles, or line lights, disposed about element 20. Another preferred such lighting source 24 is a ring light and, still more preferably, a ring light of the type disclosed in commonly assigned U.S. Pat. No. 5,367,439. The lighting source 24 is positioned to illuminate the lead area of the frame 20 in such a way to cause potential defects thereon (eg., adhesive patches) to appear as light features against a dark background.

Other lighting sources known in the art can be used in place of on-axis source 22 and ring light source 24 to illuminate a surface under inspection. Considerations for selection and positioning of the sources 22, 24 are that expected defects on the lead frame appear differently (if at all) with respect to the background when illuminated by each respective source 22, 24.

More particularly, the lighting sources 22, 24 are selected and positioned such that the subtraction of an image captured by camera 26 when the lead frame is illuminated by one of the sources (e.g., 22) from an image captured by camera 26 when the lead frame is illuminated by the other source (e.g., 24) emphasizes defects on the leads, e.g., by increasing the contrast between the defects and the background (i.e., the remainder of the surface).

Put another way, the lighting sources 22, 24 are selected and positioned in such a way that an image generated by camera 26 when the lead frame is illuminated by one source has an defect-to-background contrast of an opposite polarity then the defect-to-background contrast of an image generated by camera 26 when the lead frame is illuminated the other source.

Thus, for example, in a preferred arrangement to detect adhesive on lead (AOL) defects on the lead frame 20, the on-axis lighting source 22 is selected and positioned (in relation to frame 20 and mirror 28) to cause a defect to be dark on a light background (e.g., "negative" defect-to-background contrast polarity), while the diffuse ring light 24 is selected and positioned to make the same defect appear light on a dark background (e.g., "positive" defect-to-background contrast polarity).

Figure 3A:
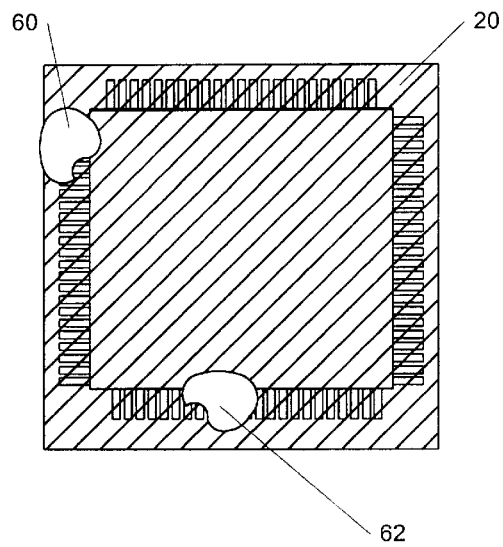
FIGS. 3A–3C depict sample images (and their difference images) generated by the lighting arrangement shown in FIG. 2A.

FIG. 3A similarly depicts an image generated by camera 26 when a lead frame 20 with AOL is illuminated by ring light or grazing light source 24. As shown in the illustration, the ring/grazing light reveals the adhesive as light patches 60, 62 on a dark background.

Figure 3B:
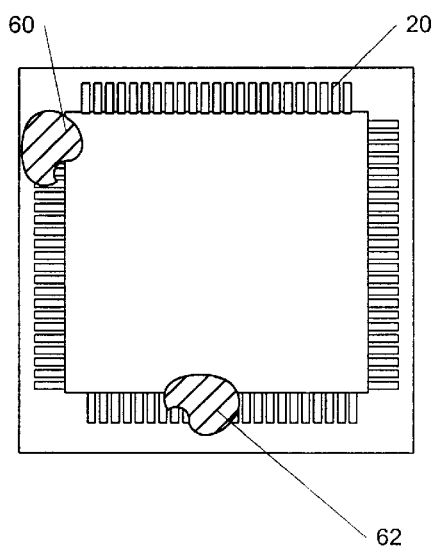

FIG. 3B depicts an image of the type generated by camera 26 when the same lead frame is illuminated by on-axis lighting source 22. As shown in FIG. 3A, the on-axis lighting reveals adhesive 60, 62, on the leads as dark patches on a light background.

Figure 3C:
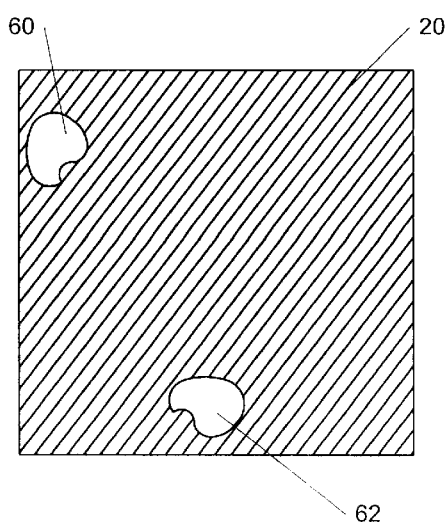

FIG. 3C reveals a result according to the invention of subtracting the images generated by camera 26 under these two separate lighting conditions. Put another way, FIG. 3C represents the result of subtracting the image of FIG. 3B from the image of FIG. 3A. In FIG. 3C, the adhesive on the lead frame 20 is revealed as very light patches against a very dark background. (Note that this figure shows the output of the subtraction after remapping step 114, described below.)

Figure 4:
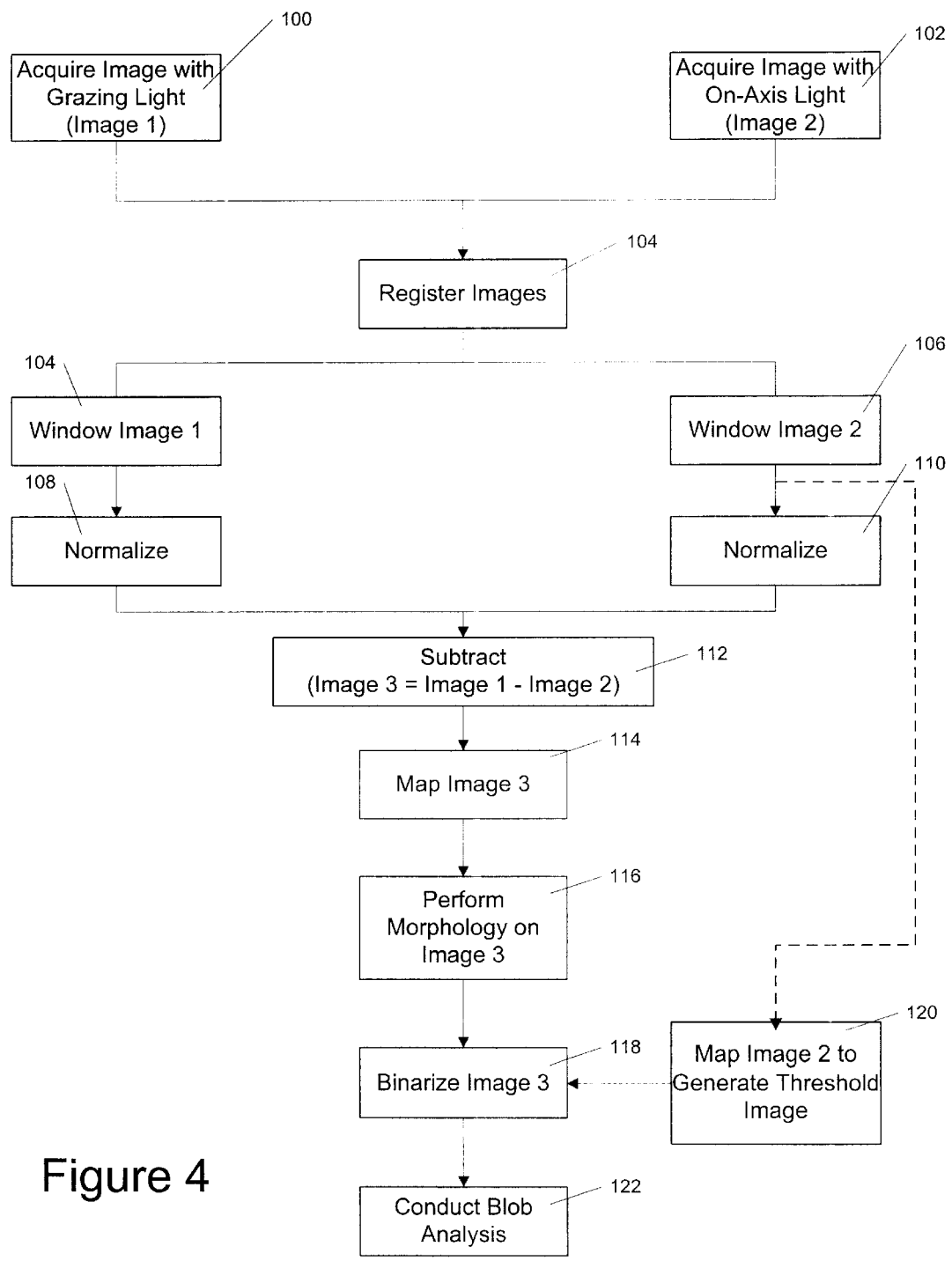
FIG. 4 depicts a methodology for semiconductor die lead frame inspection according to the invention.

FIG. 4 illustrates a method for inspecting semiconductor lead frames according to the invention. In step 100, the method acquires an image of the lead frame with lighting source 24 or other grazing light. Likewise, in step 102, the method acquires an image of the lead frame with on-axis light source 22. Though these images can be acquired at any times—though not concurrently—they are typically acquired at about the same time. This reduces the risk that the lead frame will be moved between acquisitions and, thereby, removes the need to register the images.

In the discussion that follows, the image acquired in step 100 is referred to as "Image 1," while the image acquired in step 102 is referred to as "Image 2." Although the discussion herein is directed toward subtraction of Image 2 from Image 1, those skilled in the art will likewise appreciate that Image 1 can be subtracted from Image 2. Preferably, Image 2 is subtracted from Image 1 in instances where the object is lighter than the background in Image 1, and where object is darker than the background in Image 2. Conversely, Image 1 is preferably subtracted from Image 2 in instances where the object is lighter than the background in Image 2, and where object is darker than the background in Image 1.

In optional step 104, the method registers the images to insure alignment of the features therein. Though not necessary in many instances, this step is utilized if the lead frame or camera is moved between image acquisitions. Image registration can be performed, for example, by a two-dimensional cross-correlation of images, in the manner disclosed in Jain, *Fundamentals of Digital Image Processing*. (Prentice Hall 1989) at Chapter 2, the teachings of which are incorporated herein by reference.

In steps 104 and 106, the method windows Images 1 and 2. These steps, which are optional, reduce the area (or pixels) of the respective images under consideration and, thereby, reduce processing time and/or computational resources. These steps can be performed by selecting the relevant subset of the pixel array of each image.

In steps 108 and 110, the method normalizes the (windowed) images. These optional steps, which compensate for overall differences in image intensity, can be performed by any technique known in the art. Preferably, however, normalization is global, using a map derived from the global statistics of the (windowed) images. The map is defined to match the extrema (or tails) of the statistical distributions of both images.

In step 112, the method generates a difference image, Image 3, by subtracting Image 2 from Image 1. This subtraction is performed in the conventional manner known in the art. Objects in Image 3, i.e., the "difference" image, can be isolated by standard machine vision segmentation techniques such as connectivity analysis, edge detection and/or tracking, and by thresholding.

In step 114, the method maps Image 3 to remove any negative difference values (i.e. negative pixel values) resulting from the subtraction. It also can be used to normalize (or rescale) the difference image to facilitate later stages of processing. This step, which can be performed in a conventional manner known in the art, is optional.

In step 116, the method performs morphology on the difference image. Morphology, which is well known in the art, is a technique for eliminating or accentuating data in the difference image, e.g., by filtering out of variations due to video noise or small defects. This can be performed, for example in a manner disclosed by Jain, supra, at Chapter 9.9, the teachings of which are incorporated herein by reference.

In step 118, the method thresholds, or binarizes, the image to distinguish or isolate defects of interest—e.g., images of adhesive patches—from the background. Thresholding can be performed in the conventional manner known in the art. Thus, for example, a single threshold intensity value can be determined from a histogram of Image 3. Preferably, however, the threshold intensity value is predetermined, i.e., based on empirical analysis of prior images.

In certain applications, use of a high global threshold intensity value will result in portions of the object of interest being interpreted as background and, therefore, will result in poor segmentation. Likewise, use of a low global threshold intensity value will result in background being interpreted as objects of interest. To overcome this, the method includes an optional step of thresholding using a threshold image generated by mapping Image 2; see step 120. That threshold image is made up of pixels representing local threshold values.

In instances where a threshold image is used, binarization step 118 involves subtracting the threshold image from Image 3, then, mapping positive differences to 1 (indicating object) and negative differences to zero (indicating background).

Following binarization, the method of step 122 conducts connectivity analysis to determine the properties of any defects in the binarized image. Those properties, which include size, position orientation, and principal moments, can be used to determine whether the defect necessitates rejection of the lead frame.

Figure 2B:
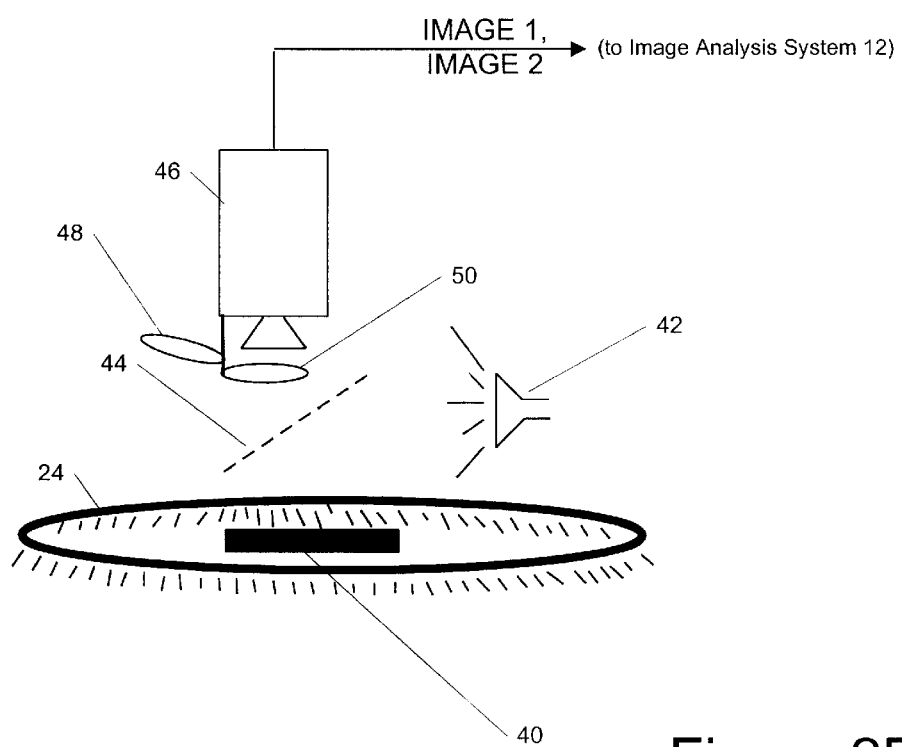

In further embodiments, the invention contemplates an image capture arrangement as shown in FIG. 2B. Here, rather than employing two lighting sources, a system according to the invention captures light reflected from the element 40 under inspection in two different wavelengths. For this purpose, the lead frame is illuminated by a single light source 42, which can be, for example, a white light. Reflections from the lead frame captured by camera 26 can be filtered to capture the differing wavelengths. Such filtering can be provided, e.g., by filters 48, 50, which are selected such that objects on the surface of element 40 appear differently (if at all) with respect to the background when the filtered light is captured by the camera 46.

In addition to capturing light of differing wavelengths, filters 48 and 50 can capture light of differing orientations. To this end, they can be polarizing lens of differing orientation for capturing light from source 42 (which may also be polarized) that is reflected off the lead frame.

The embodiments discussed above are drawn to the inspection of semiconductor die lead frames. It would be within the capability of one of ordinary skill in the art to apply these teachings to the inspection of semiconductor die surfaces without departing from the spirit and scope of the invention. Indeed, commonly assigned U.S. Pat. No. 5,949,901, the teachings of which are incorporated herein by reference, discloses the inspection of semiconductor die surfaces using the same techniques as those described herein.

Described above are machine vision methods meeting the objects set forth. These methods provide improved machine vision semiconductor lead frame inspection overcoming the deficiencies of the prior art segmentation techniques, such as GTC. For example, apart from instances where an illuminated object is moved between image captures, the method does not require registration of images prior to subtraction. Nor the method require training. Still further, the method is applicable to the wide range of repeatable and nonrepeatable images. Yet still further, the methods hereof permit inspection of the full range of lead frame types, including flying/free lead configurations, even where the lead count is high. Moreover, these methods do not consume excessive memory or processing time, even in instances where the package under inspection is rotated.

It will be appreciated that the embodiments described above are illustrative only and that additional embodiments within the ken of those of ordinary skill in the art fall within the scope of the invention. By way of example, although the discussion herein primarily refers to subtraction of Image 2 from Image 1, those skilled in the art will likewise appreciate that Image 1 can, alternatively, be subtracted from Image 2 with like success (albeit with a reversal of "polarity" in the resulting image).

We claim:

1. A machine vision method for inspecting a substantially flat surface, the method comprising:

generating with a digital camera a first image of the substantially flat surface and a defect thereon;

generating with the digital camera a second image of the substantially flat surface and the defect thereon, such that the defect in the second image is of a different contrast polarity with respect to the substantially flat surface than the defect in the first image with respect to the substantially flat surface;

comparing, for the purpose of contrast enhancement of reflectivity features of the defect with respect to the substantially flat surface, each pixel of the second image to each corresponding pixel of the first image;

generating a third image representing results of comparing each pixel; and isolating the defect using the third image.

2. A method according to claim 1, where isolating comprises:

performing connectivity analysis on the third image to distinguish the defect from the substantially flat surface.

3. A method according to claim 1, wherein isolating comprises:

detecting and tracking edges in the third image to isolate the defect.

4. A method according to claim 1, wherein the isolating step includes:

thresholding the third image to distinguish at least one of a defect and its edges from the substantially flat surface.

5. A method according to claim 4, wherein thresholding comprises:

determining an intensity threshold value that distinguishes at least one of the defect and its edges from the the substantially flat surface.

6. A method according to claim 4, comprising:

generating a threshold image from at least one of the first and second images, the threshold image having pixels representing local threshold intensity values; and using the threshold image to distinguish, in the third image, at least one of the defect and its edges from the substantially flat surface.

7. A method according to claim 6, wherein the step of generating the threshold image includes the step of mapping image intensity values in the second image to generate the threshold image.

8. A method according to claim 6, wherein the step of using the threshold image includes the step of subtracting the threshold image from the third image.

9. A method according to claim 1, further comprising:

normalizing at least one of the first and second images before comparing.

10. A method according to 9, wherein the normalizing step includes the steps of determining distributions of intensity values of each of the first and second images;

generating a mapping function for matching extrema of those distributions; and transforming the intensity values of at least one of the first and second images with that mapping function.

11. A method according to claim 1, including:

generating the first and second images by illuminating the substantially flat surface with different respective emission sources.

12. A method according to claim 1, including the step of generating the first and second images with light of different respective polarizations.

13. A method according to claim 1, including:

generating the first and second images by illuminating the substantially flat surface with emissions in different respective wavelengths.

14. A method according to claim 1, wherein generating the first image includes the step of illuminating the substantially flat surface with a light source selected from the group of light sources including a direct light source and a grazing light source; and generating the second image includes illuminating the substantially flat surface with the other light source in that group.

15. A method according to claim 1, further comprising:

registering the first and second images with one another before comparing.

* * * * *